US008225638B1

(12) United States Patent
Ardiff et al.

(10) Patent No.: US 8,225,638 B1
(45) Date of Patent: Jul. 24, 2012

(54) METHODS TO DETERMINE THE DURABILITY AND WEAR-RESISTANCE OF SOFT ARMOR

(75) Inventors: Henry G. Ardiff, Chesterfield, VA (US);
David A. Hurst, Richmond, VA (US);
Duane R. Prior, Richmond, VA (US);
Brian H. Waring, Chester, VA (US);
Lori L. Wagner, Richmond, VA (US);
Carolyn S. Westmark, Richmond, VA (US)

(73) Assignee: Honeywell International, Inc., Morristown, NJ (US)

( * ) Notice: Subject to any disclaimer, the term of this patent is extended or adjusted under 35 U.S.C. 154(b) by 1310 days.

(21) Appl. No.: 11/876,041

(22) Filed: Oct. 22, 2007

(51) Int. Cl.
*G01N 3/56* (2006.01)
(52) U.S. Cl. .............................................................. 73/7
(58) Field of Classification Search .................. 73/7, 159
See application file for complete search history.

(56) References Cited

U.S. PATENT DOCUMENTS

| | | | | |
|---|---|---|---|---|
| 2,323,175 | A | * | 6/1943 | Young et al. ......................... 73/7 |
| 2,519,551 | A | * | 8/1950 | Cross et al. .......................... 73/7 |
| 2,670,627 | A | * | 3/1954 | Shaw ............................... 73/159 |
| 2,696,736 | A | * | 12/1954 | Frederick ........................ 73/159 |
| 3,387,484 | A | * | 6/1968 | Ainslie ................................ 73/7 |
| 3,641,807 | A | * | 2/1972 | Brooks ................................ 73/7 |
| 4,012,815 | A | | 3/1977 | Benzaquen ...................... 26/28 |
| 4,140,827 | A | | 2/1979 | Willwerth et al. ............. 428/151 |
| 4,233,012 | A | | 11/1980 | Willwerth et al. ............ 425/162 |
| 4,403,499 | A | | 9/1983 | Sack et al. |
| 7,179,343 | B2 | | 2/2007 | VanEperen et al. ........... 156/163 |

FOREIGN PATENT DOCUMENTS

| JP | 58-100737 A | 6/1983 |
|---|---|---|
| JP | 05-240760 A | 9/1993 |

* cited by examiner

*Primary Examiner* — John Fitzgerald

(57) ABSTRACT

Methods to determine the durability and wear-resistance of soft armor. Observations on field tested articles of soft body armor indicate that the materials are subject to a combination of flexing, tensile, compressive and abrasive forces. The forces and stresses to which soft armor articles are subjected to can be duplicated in a controlled, isolated, measurable, appropriate and intuitive manner, to correlate ballistic performance with durability and wear characteristics. The tests closely approximate the forces and stresses experienced in the end use of ballistic resistant composite articles.

25 Claims, 5 Drawing Sheets

METHODS TO DETERMINE THE DURABILITY AND WEAR-RESISTANCE OF SOFT ARMOR

BACKGROUND OF THE INVENTION

1. Field of the Invention

This invention relates to methods to determine the durability and wear-resistance of fabrics and soft armor.

2. Description of the Related Art

Soft body armor used by military and law enforcement organizations is subject to criteria not imposed on hard armor products. Particularly, the National Institute of Justice (NIJ), through their Technology Assessment Program (TAP), operates a body armor testing program to ensure that protective equipment worn by law enforcement personnel meets NIJ-established minimum performance requirements. Among the specific criteria are requirements for durability and wear-resistance. There are currently no accepted test methods specifically designed to gauge these properties for soft body armor. The incumbent methods are borrowed from other textile industries and tend to test and measure the effect of stresses on single layers of a composite. Results are then scaled to draw conclusions on the characteristics of an assembled multi-layer article. Such extrapolation can be inaccurate and can cause misconceptions about the performance of a multi-layer composite. Direct measurement of these durability and wear-resistance characteristics on the assembled multi-layer composite would lead to more accurate conclusions.

The lack of armor specific test protocols for durability and wear-resistance has led to the use and acceptance of inappropriate test methods that accelerate the effect of a mechanical influence on an article. These types of tests tend to fall into two categories. The first category are those tests that exaggerate the forces and conditions imposed on an article with the intention of forcing failure. The second category of tests uses appropriately scaled forces and conditions and cycles the article through a very large number of perturbations in a condensed period of time. Appropriately scaled forces will give a more realistic gauge of the expected performance of an article.

Based on observations of the condition and appearance of soft body armor that has been exposed to varying lengths of field service, generalizations can be made as to the nature of the forces and stresses that the articles have experienced. The subsequent impact of these perturbations on the ballistic performance of the article is measurable. Observations on field tested articles of soft body armor indicate that the materials are subject to a combination of flexing, tensile, compressive and abrasive forces. The methods of the present invention can duplicate those forces and stresses in a controlled, isolated, measurable, appropriate and intuitive manner to correlate ballistic performance with durability and wear characteristics. These tests and testing apparatuses are designed to achieve close approximation of the forces experienced in the end use of ballistic resistant composite articles.

SUMMARY OF THE INVENTION

The invention provides an apparatus for testing a frictional wear property of a flexible fabric comprising:
a) a stationary roller assembly comprising a supporting frame, and a plurality of adjacently spaced rollers mounted on the supporting frame; each roller having a central longitudinal axis that is positioned parallel to the central longitudinal axis of the other roller or rollers; each of said rollers being mounted on the supporting frame for rotation around its central longitudinal axis; wherein adjacent rollers are spaced from each other to define a space therebetween that allows a flexible fabric to be translated therethrough; the supporting frame being either attached to or an integral component of a structural framework;
b) at least two opposing mounts for releasably supporting a flexible fabric to be tested in the space or spaces between adjacent rollers and in a position for frictional engagement of the flexible fabric with the rollers; and
c) a reciprocating driver connected to the mounts for automatically and continuously translating the mounts back and forth along a path such that when a flexible fabric is supported by the mounts, the flexible fabric is positioned for passing through the space or spaces between the plurality of rollers and in frictional engagement with the rollers.

The invention also provides a process for evaluating a frictional wear property of a flexible fabric, comprising:
a) providing a roller assembly comprising a supporting frame and a plurality of adjacently spaced rollers mounted on the supporting frame; each roller having a central longitudinal axis that is positioned parallel to the central longitudinal axis of the other roller or rollers; each of said rollers being mounted on the supporting frame for rotation around its central longitudinal axis; wherein adjacent rollers are spaced from each other to define a space therebetween that allows a flexible fabric to be translated therethrough; the supporting frame being either mounted on, attached to or an integral component of a structural framework;
b) positioning a flexible fabric through the space or spaces between adjacent rollers, which flexible fabric is releasably supported in said space or spaces between adjacent rollers and in a position for frictional engagement with the rollers, by at least two opposing mounts; and
c) effecting an automatic and continuous reciprocating translation of the flexible fabric back and forth through the space or spaces between the adjacent rollers along a path, under conditions sufficient to cause wear of the flexible fabric.

The invention further provides an apparatus for testing a frictional wear property of a flexible fabric comprising:
a) a roller assembly comprising a supporting frame and a plurality of adjacently spaced rollers mounted on the supporting frame; each roller having a central longitudinal axis that is positioned parallel to the central longitudinal axis of the other roller or rollers; each of said rollers being mounted on the supporting frame for rotation around its central longitudinal axis; wherein adjacent rollers are spaced from each other to define a space therebetween that allows a flexible fabric to be translated therethrough; the supporting frame being mounted on a structural framework;
b) at least two opposing stationary mounts for releasably supporting a flexible fabric to be tested in the space or spaces between adjacent rollers and in a position for frictional engagement of the flexible fabric with the rollers; and
c) a reciprocating driver connected to the roller assembly for automatically and continuously translating the roller assembly back and forth along a path such that when a flexible fabric is supported by the mounts, the flexible fabric is positioned for passing through the space or spaces between the plurality of rollers and in frictional engagement with the rollers.

DETAILED DESCRIPTION OF THE INVENTION

Figure 1:
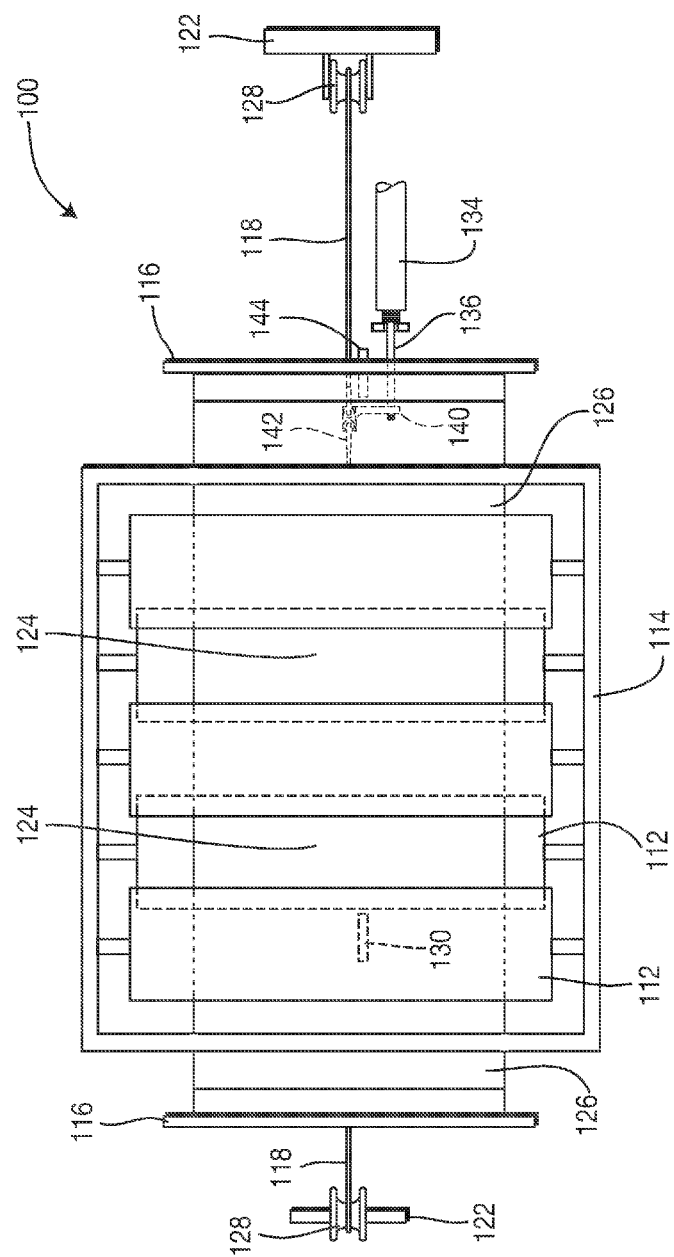
FIG. 1 is a front-view schematic representation of a section of an apparatus of the invention that includes a stationary roller assembly.
Figure 2:
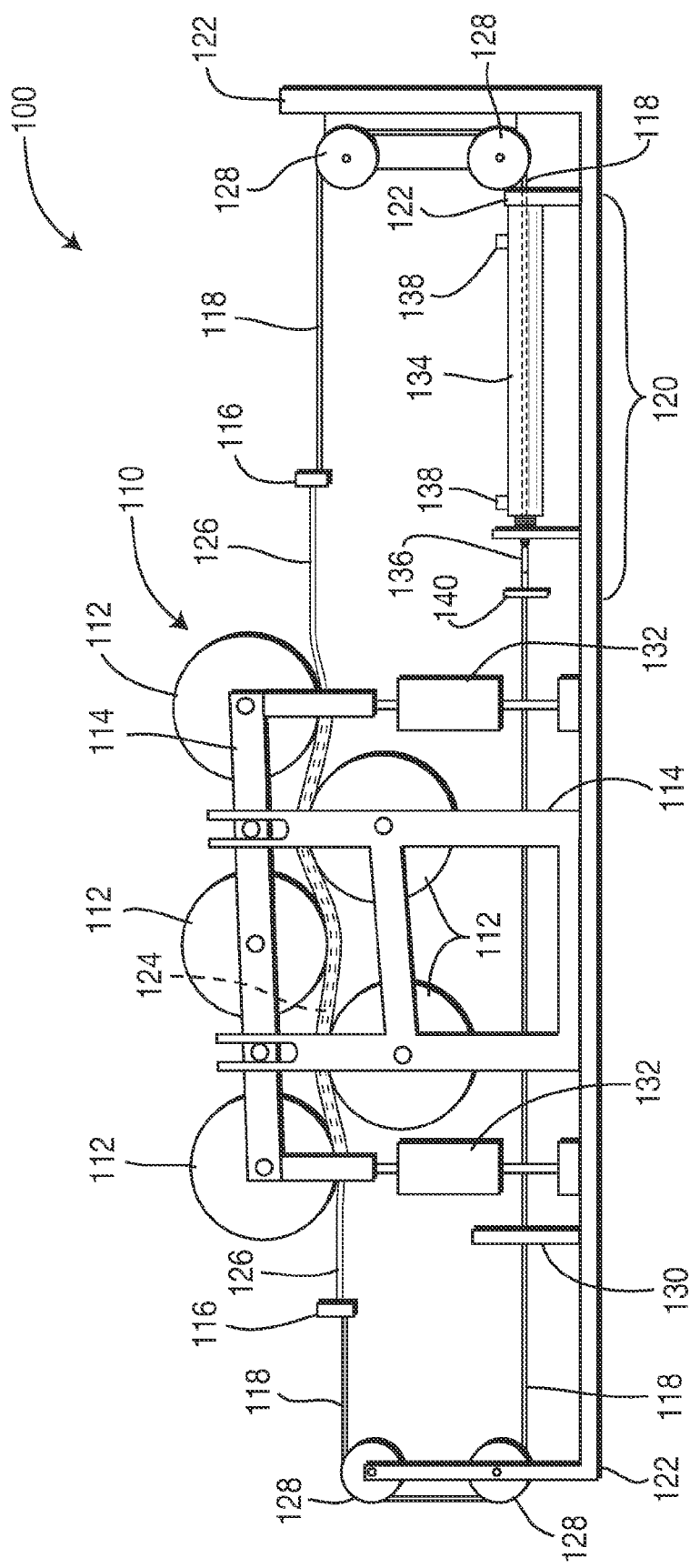
FIG. 2 is a side-view schematic representation of a section of an apparatus of the invention that includes a stationary roller assembly and a carrier pouch.

As illustrated in FIG. 1 and FIG. 2, a testing apparatus 100 is provided that gauges the durability and wear resistance of flexible fabrics that are used to produce soft body armor. Testing apparatus 100 includes a stationary roller assembly 110 that includes a plurality of adjacently spaced rollers 112 mounted on a supporting frame 114. The number of rollers 112 may vary, but the roller assembly 110 includes at least two rollers 112, preferably at least four rollers 112. FIGS. 1 and 2 show an embodiment that includes five rollers. Each of the rollers 112 has a central longitudinal axis that is positioned parallel to the central longitudinal axis of the other roller or rollers 112, and each of the rollers 112 are mounted on the supporting frame 114 for rotation around its central longitudinal axis. The radius of each roller is preferably from about ⅛ inch (3.175 mm) to about 24 inches (60.96 cm), most preferably from about ¼ inch (6.35 mm) to about 2 inches (5.08 cm).

As shown most clearly in FIG. 2, adjacent rollers 112 are spaced from each other to define a space therebetween that allows a flexible fabric to be translated therethrough. To increase the fabric wrap angle, the rollers are moved towards each other, and to maximize the wrap angle adjacent rollers are positioned as close together as practicable without pinching the test fabric. Accordingly, the minimum preferred distance separating adjacent rollers is about equivalent to thickness of the fabric test sample. The distance between adjacent rollers may be fixed or adjustable. When adjustable, the distance is adjusted by positioning a movable roller(s) relative to a fixed roller(s). Moveable rollers are typically attached to a common frame and positioned by height regulators 132. Height regulators 132 may be manually controlled, electrically controlled, pneumatically controlled, or controlled by any other suitable means as would be determined by one skilled in the art. In one embodiment, the position of the common frame may be controlled by guide pins. In another embodiment, the common frame may be controlled by pneumatically controlled air cylinders as in FIG. 2. As illustrated in FIG. 2, air cylinders 132 move a common frame to open and close the space between the rollers for fabric access and gap adjustment. Similar to air cylinder 134 (described below), air cylinders 132 are preferably controlled by an air pressure controlled, pneumatic control system whereby they are connected to a pneumatic circuit comprising a pressure sensor that detects changes in air pressure. Alternately, air cylinders 132 may be hydraulic cylinders that are controlled by a hydraulic fluid rather than air.

Figure 4:
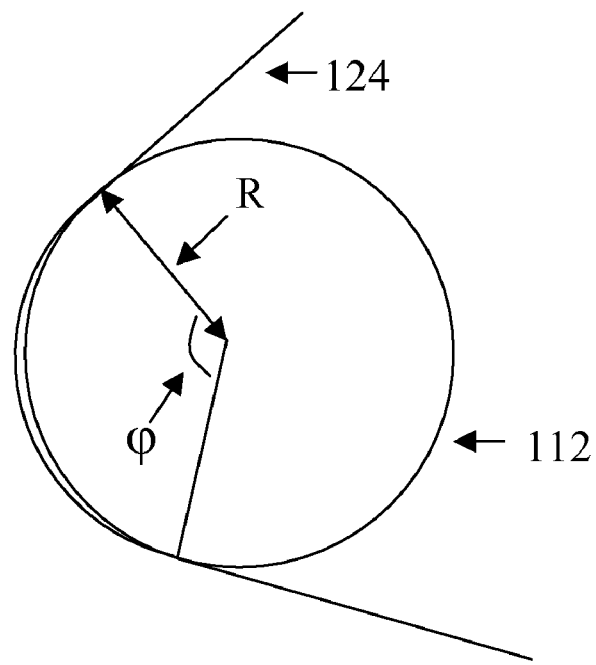
FIG. 4 is a side-view schematic representation of a fabric wrapping around a roller, illustrating the wrap angle and bend radius.

The preferred alignment of the rollers 112 of roller assembly 110 is illustrated in FIG. 2. Adjacent rollers 112 are preferably positioned in an offset position relative to one another such that a flexible fabric is turned in an under/over alternating pattern at a wrap angle of from about 1 degree to about 180 degrees as it traverses through the rollers. More preferably, adjacent rollers 112 are positioned in an inter-penetrating, offset position relative to one another such that a flexible fabric is turned at a wrap angle of from about 45 degrees to about 180 degrees, and most preferably at a wrap angle of from about 110 degrees to about 180 degrees as it traverses through the rollers. As used herein, "inter-penetrating" rollers are characterized by an overlap of a lateral plane at the lowest point of one roller with a lateral plane at the highest point of an adjacent roller, causing the fabric to contact both rollers and bend as is traverses in a space between said rollers. Inter-penetrating rollers are shown in FIG. 2. As used herein, the "wrap angle" ($\phi$) is defined as the cumulative angular contact of the test specimen against the friction-inducing device (roller) expressed in radians or degrees. The wrap angle (in units of radians) can be calculated by measuring the arc length of the fabric that is in contact with the roller and dividing by the radius of the roller. Similarly, the wrap angle (in units of degrees) can be calculated by multiplying the wrap angle in radians by a factor of $\pi/180$. The term "bend radius" ("R") is defined herein as the radius of a roller, which directly affects the wrap angle, as illustrated in FIG. 4. A high wrap angle provides more aggressive conditions than a low wrap angle, and a low bend radius provides more aggressive conditions than a high bend radius, thereby effectively simulating fabric wear in a real life aggressive environment.

Each portion of the fabric will thereby experience bending in two directions (up and down in a horizontal set-up). Should the fabric then be rotated in its plane and the test repeated, an additional group of stresses would be introduced. For example, the fabric could be rotated 90° in its plane to introduce a second set of stresses, and then rotated 45° in its plane to introduce a third set of stresses. The fabric can then be evaluated for visual signs of durability and mechanical wear, i.e. wear caused by the testing apparatus due to friction, fabric abrasion or fabric bending. Ballistic testing of the fabric compared to a control sample will allow the correlation of the number of test cycles, the visual appearance and the ballistic performance. In addition, the surface or surfaces of one or more of rollers 112 may be textured to increase fabric abrasion as it engages rollers 112. Alternately, the apparatus 100 may further include one or more non-rotating abrasion bars positioned adjacent to at least one of the rollers, or substituted in place of one or more of the rollers, to abrade the fabrics. The non-rotating abrasion bar or bars increase surface friction and offer a sharper fabric bend radius, about 0.03 inch (0.762 mm) to about 0.12 inch (3.048 mm), compared to rollers alone, allowing a wrap angle of close to 180°. The abrasion bar(s) can be of various cross-sectional shapes and surface textures to increase or decrease the severity of abrasion. Fabric abrasion serves to simulate actual frictional wear of a fabric article that can result from an object rubbing up against the article, such as the rubbing of a weapon holster or utility belt against a bullet resistant vest.

In the method of the invention utilizing apparatus 100, a fabric 124 is tested by positioning the fabric 124 through a space (when there are only two rollers) or spaces (when there are more than two rollers) between adjacent rollers 112 and effecting the automatic and continuous reciprocating movement of the fabric 124 back and forth through the space or spaces between the adjacent rollers 112 along a path under conditions sufficient to cause wear of the fabric 124. This "path" is most preferably a substantially straight linear path.

For apparatus 100, the movement of the fabric 124 is effected by the back and forth translation of opposing mounts 116. As is most clearly shown in FIG. 1, testing assembly 100 includes at least two opposing mounts 116 that are positioned such that at least one mount is positioned on each of two opposite sides of the roller assembly. Mounts 116 support the fabric 124 in a position between the adjacent rollers 112 while the fabric 124 is concurrently in frictional engagement with the adjacent rollers 112. Mounts 116 may support the fabric 124 between the rollers either directly or indirectly. For direct support, fabric 124 is directly in contact with and attached to mounts 116. Importantly, mounts 116 releasably hold or support fabric 124 in position between the rollers, so that the fabric may be easily removed for measurement of wear resistance and durability properties. For indirect support, fabric 124 is held in a carrier pouch 126 and the carrier pouch 126 is directly in contact with and attached to mounts 116. In the preferred embodiment of the invention, fabric 124 is indirectly supported by mounts 116. Fabric 124 is preferably centrally located within carrier pouch 126, and fabric sample 124 is approximately one third of the length of the carrier pouch 126. This allows a complete fabric sample to traverse completely through all of the rollers from one end to the other end, achieving a full bending cycle on the entire fabric sample instead of just a portion of the sample, and subjects the entire surface of the test sample to the full number of bending cycles per stroke. Mounts 116 may comprise mounts that clamp on the testing sample and hold it in place, or may be a bar, post or other support structure to which a fabric 124 or carrier pouch 126 is attached via any suitable means as would be readily determined by one skilled in the art, such as with clips or other suitable fasteners.

Carrier pouch 126 may be formed from any suitable polymeric material, such as nylon, and may be a discreet and detachable object or may be an integral, non-detachable component of apparatus 100. Most preferably, carrier pouch 126 is formed from rip-stop nylon. Rip-stop nylon is a lightweight, woven nylon fabric including inter-woven rip-stop reinforcement threads in a crosshatch pattern to improve tear resistance. Rip-stop nylon is a conventionally known material and is commercially available, for example, from Busch and Associates, LTD. of Newport Beach, Calif. When the carrier pouch 126 is present, a fabric 124 is releasably held within the carrier pouch 126 between the rollers, so that the fabric may be easily removed from the pouch for measurement of wear resistance and durability properties.

Fabric sample 124 may comprise one or more layers of woven ballistic resistant fabrics, non-woven ballistic resistant fabrics or a combination thereof. The fabric 124 may generally have any shape and may comprise a fabric article, such as a vest, or a portion of a fabric article. Such materials are well known in the art, and are described, for example, in U.S. Pat. Nos. 4,403,012, 4,457,985, 4,613,535, 4,623,574, 4,650,710, 4,737,402, 4,748,064, 5,552,208, 5,587,230, 6,642,159, 6,841,492, 6,846,758, all of which are incorporated herein by reference.

The wear testing method of the invention may be performed on a simple fabric sheet or on an end article, such as an assembled ballistic resistant vest. Most preferably, the fabric 124 is a multilayer fabric sample, such as a multilayer piece of fabric or a multilayer assembled ballistic resistant article, because this will most accurately simulate the abrasion profile experienced in a multi-layer ballistic resistant article in actual use. A multilayer fabric sample may include multiple layers that are attached to each other, such as by stitching, or the layers may be stacked on each other without being attached. Preferably, a fabric sample 124 to be tested includes a plurality of stacked, unattached fabric layers, each of which are preferably from about 6 inches to about 36 inches (15.24 cm to about 91.44 cm) in both length and width, more preferably from about 12 inches to about 24 inches (30.48 cm to about 60.96 cm) in both length and width. The fabric samples 124 may be of any shape, but are preferably rectangular or in the shape of a ballistic vest pattern. When used, carrier pouch 126 is preferably of a greater length than the fabric, most preferably about twice the length of the fabric sample plus the length of the serpentine contact path between the rollers, allowing the fabric to be fully contained within the pouch and for the pouch to be attached to both of said opposing mounts 116. This length may vary depending on the specifications of the apparatus 100 and would be readily determined by one skilled in the art. The carrier pouch 126 is preferably about 0.5 cm to about 1.0 cm greater in width than the fabric being held inside said pouch. This carrier pouch width may also vary but is most preferably not greater than 1.0 cm greater in width, as such excess width is not needed.

The fabric 124 may be loosely placed within the carrier pouch 126 or may be stitched to or otherwise attached to the pouch 126. In the preferred process of the invention, the fabric 124 and carrier pouch 126 are stitched together. Stitching serves to prevent layers of a stacked, unattached multilayer fabric sample 124 from moving relative to one another during the test, thereby inhibiting interlayer abrasion. Accordingly, less stitching allows more interlayer abrasion. For example, the carrier pouch may be centered within the pouch and then stitched to the pouch across the entire width of the fabric at the longitudinal center of the fabric. This also prevents the fabric 124 from slipping within the pouch 126 or falling to the end of the pouch 126 during testing. Alternately, the fabric 124 may be centered within the pouch and held in place by stitching the bottom edge and/or top edge of the fabric 124 to the pouch 126. The stitching may be straight across the fabric/pouch or may be stitched in a pattern to simulate the stitching of an actual ballistic vest construction design. In an actual vest incorporating a multilayer protective fabric, there is typically some movement and friction of the layers against each other. The amount of movement between adjacent individual layers of ballistic fabric relative to one another when the vest is flexed is highly dependent on the pattern and degree of stitching of the vest layers to one another. Importantly, this test method allows the levels of damage in the fabric sample 124 to be quantified using industry-accepted methods, such as a $V_{50}$ ballistic test, due to the consistent levels of damage that are achieved across the entire shoot pack.

When a fabric sample 124 is directly supported by mounts 116, the reciprocal movement of the mounts 116 will expose the fabric 124 to some degree of tension due to the tension applied on the mounts 116 by connector elements 118. This may limit the freedom of movement of component fabric layers of fabric 124 (in the case of a multilayer fabric sample) against each other. This tension on the fabric is controlled by controlling the tension applied to the mounts 116, and could be very low or relatively high. The method of the invention has been found to cause the most realistic damage to the fabric when there is negligible tension on the cables that move the sample back and forth.

The method of the invention is useful for both a fabric sample 124 including multiple layers of fabric or only a single layer of fabric. However, the greatest utility of the inventive method is expected to be in testing multiple layers. The layers may be unattached, or they may be stitched or otherwise bonded together. However, the most significant interlayer abrasion will occur when the layers are not attached or bonded together. To most accurately simulate the natural use of a ballistic resistant article, it is desired that the fabric layer or layers have some freedom of movement against other layers or against a carrier pouch.

Further, testing the fabric sample 124 in a carrier pouch 126 without tension allows the samples 124 to be pulled through the rollers on a bias angle (at an angle that is not parallel to the direction of either the warp or fill fibers in the sample), enhancing damage to the fabric. Fabric abrasion may also be enhanced, for example, by adding lengthwise or circumferential ribs to the rollers (see FIG. 5A), by inducing creases into a test sample before putting it into the machine, or by pre-treating the fabric by exposure to environmental stressors such as elevated or low temperatures, humidity, or immersion in water or other liquids. Ribs may be added, for example, by adhering strips of plastic, wood, or other materials to a roller along its length, by adhering a durable ring to the roller, machining the roller such that it has raised ribs when the roller is produced, or, for example, by wrapping strips of tape, such as masking tape, around the roller circumference in one or more locations on the roller (see FIG. 5A). Other means may also be appropriate as determined by one skilled in the art. In a preferred embodiment, ribs are added to the rollers in an offset pattern to mimic fabric creasing (see FIGS. 5A and 5B).

In the most preferred embodiments of the invention, enhanced fabric abrasion is achieved by the addition of circumferential ribs to at least one roller. Circumferential ribs provide bending in a second plane that is perpendicular to the plane of bending around the rolls, essentially forming channels and forcing the fabric down into these channels and forcing the fabric to fold or crease in a direction that is out of the existing plane of the fabric (e.g. in the "z" direction, where the "z" axis passes through the thickness of the fabric sample in a direction that is perpendicular to the surface of the fabric sample). This creasing effect has been found to accurately represent the creasing of a fabric in actual use. A most accurate creasing representation is achieved when the rib "channels" are aligned at right angles to the axis of the rollers. Lengthwise ribs that are completely perpendicular to the direction of travel of the fabric generally will not give this desired creasing effect, and accordingly are not most preferred. Lengthwise ribs are useful for enhancing fabric abrasion, but may abrade the fabric more severely than circumferential ribs, and may not be an accurate simulation of actual vest wear and tear.

As illustrated in FIG. 2, supporting frame 114 of the stationary roller assembly 110 is either attached to or an integral component of a structural framework 122 that supports each of the functional components of testing assembly 100. Each of the opposing mounts 116 are connected to the structural framework 122 either directly or indirectly. Preferably, mounts 116 are indirectly connected to the structural framework 122 indirectly by at least one connector element 118. As shown in the figure, connector elements 118 preferably comprise connecting wires or a connecting cable loop. As shown in the figure, a connecting cable loop 118 is connected to mounts 116 on either side of roller assembly 114, being threaded across one or more pulleys 128, leading the wire 118 to a reciprocating driver 120, to which it is functionally connected. Opposing mounts 116 are connected to the reciprocating driver 120 by connector(s) 118. In the most preferred embodiments, reciprocating driver 120 is part of an air pressure controlled, pneumatic control system that enables the automatic and continuous pneumatic translation of the mounts 116 back and forth along a path such that the flexible fabric 124 passes through the space or spaces between the plurality of adjacently spaced rollers 112 and in frictional engagement with the rollers 112. As illustrated in FIG. 2, a preferred pneumatic reciprocating driver 120 includes an air cylinder 134 that encloses a piston (not shown). Air cylinder 134 is attached to or mounted on structural framework 122. The piston is connected to a rod 136, and rod 136 is connected to a bar 140 (see FIG. 6). Bar 140 is cantilevered off to the side of the end of the rod 136. In the apparatus embodiment of FIG. 6, connector element 118 is a cable loop; a fitting 142 is connected to each end of the cable loop 118, and each fitting is attached to bar 140 top complete the loop.

Figure 6:
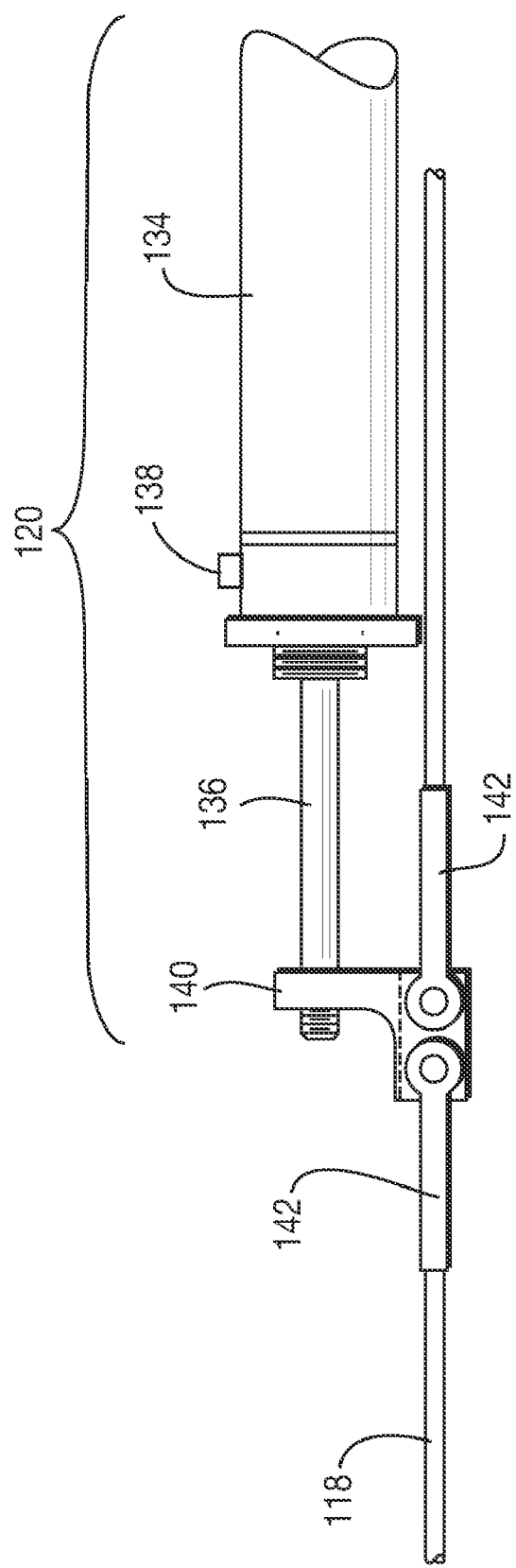
FIG. 6 is a blown-up, bottom-view schematic representation illustrating a retracted rod attached to the air cylinder of a pneumatic control system and the connection of a connecting cable loop to the control system.

As shown in FIGS. 2 and 6, an air port 138 is present at each end of the cylinder 134. Each port 138 is connected to an air source (not shown) and to a shuttle valve (not shown). The air cylinder 134 is connected to a pneumatic circuit which comprises a pressure sensor. The shuttle valves and the pneumatic circuit are housed within a control box (not shown). During operation of the apparatus, the shuttle valves shift the air under pressure inside the air cylinder 134 between the two ports 138, causing the piston to move back and forth. The port at one end will exhaust the air pressure, causing the air from the opposite end of the cylinder to push the piston toward the exhausting port. Generally, the air will drive the piston until the cantilevered bar 140 attached to rod 136 comes into contact with a first path-limiting stopper 130 which limits the travel of the rod 136 in extension. The pressure sensor will read an increase in resistance due to changes in air pressure within the air cylinder 134. As the bar 140 presses against stopper 130, the air pressure within the air cylinder 134 builds up to a pre-set level of resistance where the shuttle valve is engaged, reversing the flow of air to the ends of the cylinder and reversing the direction of the piston. The piston then travels in the reverse direction until it is completely retracted back into air cylinder 134 or until bar 140 hits a second path limiting-stopper 144, where the valve and piston direction are again reversed. This back and forth movement of the piston results in the pneumatic translation of the mounts 116 back and forth along a path, because each of mounts 116 are connected to the connecting wire which is connected to the piston via bar 140 and rod 136.

Each of stoppers 130 and 144 are either attached to or integral components of structural framework 122. Their positions on the apparatus are preferably adjustable depending on the desired travel distance of the piston. In the most preferred apparatus embodiment, the length of the cylinder stroke is pre-programmed into the control system for a specifically desired travel distance and the use of a second stopper 144 is not necessary. Additionally, in an alternate embodiment, air cylinders 134 may be hydraulic controlled cylinders that are controlled by a hydraulic fluid rather than air.

Figure 3:
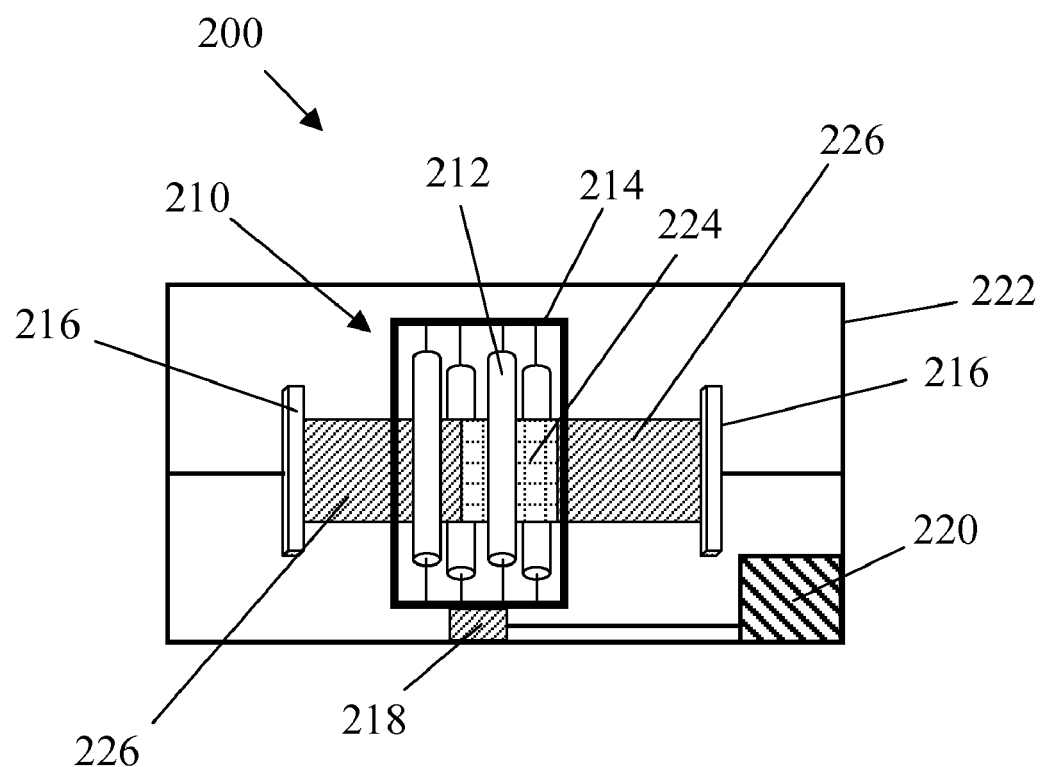
FIG. 3 is a top-view schematic representation of a section of an apparatus of the invention that includes stationary mounts and a carrier pouch.

FIG. 3 illustrates an alternate apparatus 200 of the invention. Similar to apparatus 100, apparatus 200 includes a roller assembly 210 that comprises a plurality of adjacently spaced rollers 212 mounted on a supporting frame 214, and at least two opposing mounts 216 for releasably supporting a flexible fabric 224 to be tested in a space or spaces between adjacent rollers. However, in apparatus 200 opposing mounts 216 are stationary and translation of a fabric 224 back and forth through a space or spaces between the adjacent rollers 212 is effected by automatically and continuously translating the roller assembly 210 back and forth instead of mounts 216, while mounts 216 remain stationary. In this apparatus, roller assembly 210 is moveably mounted on a structural framework 222 via an adapter 218. In said apparatus 200, adapter 218 also connects the roller assembly 210 to a reciprocating driver 220 for automatically and continuously translating the roller assembly 210 back and forth along a path such that the fabric 224 passes through the space or spaces between the plurality of adjacently spaced rollers 212 and in frictional engagement with the rollers 212.

In either method, the operation of either apparatus 100 or apparatus 200 causes a flexible fabric to be mechanically worn down by passing it back and forth through a space or spaces between the spaced rollers. The number of back and forth cycles required to cause wear to a fabric sample 124 is an independent variable and may be any number desired by the operator running the test. Typically it will be a specified number, such as 10,000 or 50,000 cycles, at which the user wishes to measure damage accumulation. Cycle speed is generally about 1 cycle per 6-8 seconds (about 12-17 inches/second) where a "cycle" is defined as the fabric passing through all the rollers in one direction (e.g. up or down). As stated previously, roller spacing is adjustable to provide the desired wrap angle.

Subsequently, the fabric is detached from the mounts 116, or removed from carrier pouch 126, and the wear of the flexible fabric is measured. Wear of the fabric may be measured, for example, by conducting well known ballistic tests such as $V_{50}$, $V_0$, back face strain (BFS) measurement and penetration depth analysis. The $V_0$ velocity of a composite is the maximum velocity at which a specified projectile will not penetrate the composite. The $V_{50}$ velocity is the impacting velocity at which 50% of projectiles fired at the composite will penetrate the composite while 50% are stopped by the composite.

Each of these techniques are well known in the art. Physical properties, such as peel strength and tensile property measurements, may also be made on individual fabric layers of the sample using well known techniques. For each of apparatuses 100 and 200, the scale or dimensions of each of the elements of the apparatus may vary as would be readily determined by one skilled in the art. In addition, each of the component parts of apparatus 100 and/or 200 may be produced via conventional means using suitable materials. Elements such as frames 120/220, framework 122/222, stopper 130, optional stopper 144, mounts 116/216, connector 118, adapter 218, etc., are preferably metallic and capable of withstanding the weight and forces associated with the invention, as would be readily understood by one skilled in the art.

The following examples serve to illustrate the invention:

EXAMPLE 1

A flexible fabric test sample was tested in a hydraulic powered testing apparatus of the invention having five rollers as illustrated in FIGS. 1 and 2. The test sample was prepared from thirty-four layers of GOLD SHIELD® GN 2115 fabric (non-woven aramid-based fabric; water-based thermoplastic polyurethane matrix; areal weight: 112 g/m$^2$), commercially available from Honeywell International Inc. of Morristown, N.J., was prepared. The layers were cut from a large fabric sheet into rectangular pieces measuring about 49.5 inches (125.7 cm) in length and about 18.5 inches (47.0 cm) in width. The layers were stacked together and the stack was fastened at both ends by clamping their ends between aluminum mounting bars that were part of the apparatus. The stack was threaded through the rollers on the apparatus as shown in FIG. 2. Each of the aluminum clamp bars were hooked via carabiner hooks to opposite ends of a steel cable that was part of the testing apparatus.

The apparatus was positioned upright so that the test sample could be continuously translated upward and downward along a vertical linear path between the adjacently spaced rollers. The rollers were horizontally spaced so that the wrap angle of the test sample over the rollers was 50 degrees. The tension on the cable was set to apply a tension of 50 pounds per square inch (psi) (344.7 kPa) to the cable. The hydraulic drive of the apparatus was turned on and the sample was pulled vertically back and forth through the rollers for 50,000 cycles, where one cycle was a complete traverse in one direction.

After 50,000 cycles, the sample was removed and visually examined. It was noted that the front and back surfaces of the sample stack exhibited a moderate amount of abrasion damage that was most highly concentrated in the vertical center area of the sample where the sample experienced contact with the most rollers during its back and forth travel. The damage consisted of some areas with wrinkling of the surface and displacement of fibers. The appearance of the damage was consistent with the appearance of damage on the outer surface of used ballistic vests formed from similar materials due to normal wear and tear.

EXAMPLE 2

Another thirty-four layer test sample of GOLD SHIELD® GN 2115 fabric was tested in a hydraulic powered testing apparatus of the invention, similar to Example 1. In this example, the horizontal spacing of the rollers was adjusted so that the wrap angle of the test sample over the rollers was 110 degrees. The tension on the cable was adjusted so that minimal tension was applied to the cable (less than 3 psi (20.68 kPa)). The hydraulic drive was turned on and the sample was pulled vertically back and forth through the rollers for 50,000 cycles. After the test cycles were completed, the sample was removed from the apparatus and visually examined. Damage to the surface of the material was severe and extensive. Numerous areas were observed in which the fabric surface was wrinkled and abraded, and numerous areas were observed in which the fibers were displaced from their parallel arrangement.

EXAMPLE 3

A pouch for holding the ballistic material samples was constructed by sewing together two pieces of rip-stop nylon fabric (70 denier, black rip-stop nylon, commercially available from Busch and Associates, LTD). Each piece of the nylon fabric measured 49.5 inches. (125.7 cm) in length and 18.5 inches (46.99 cm) in width. The pieces were sewn together by stitching across the width of the nylon at about 1.5 inches (3.81 cm) inside the top edge of the pouch and about 15 inches (38.1 cm) inside the bottom edge of the pouch, and by stitching down the length of the nylon at about 0.75 inch (1.9 cm) inside each of the side edges. A polymeric zipper was sewn into one edge of the pouch to allow access into the interior of the pouch. The nylon pouch was clamped inside the aluminum clamp bars of an apparatus as described in Example 1.

A flexible fabric test sample was prepared from twenty-one layers of GOLD FLEX® fabric commercially available from Honeywell International Inc. (one layer=4-plies of non-woven, unidirectional aramid fiber-based tape including a styrenic block copolymer matrix material (i.e. styrene-isoprene-styrene emulsion, sold under the trademark KRATON® commercially available from Kraton Polymers of Houston, Tex.), cross-plied at 0°/90°/0°/90° and sandwiched between two polyethylene films). The layers were cut from a large fabric sheet into square pieces measuring about 15 inches (38.1 cm) in both length and width. The layers were stacked together and placed inside the rip-stop nylon pouch through the zipper opening. The areal density of the sample material was about 1.0 lb/ft² (4.88 kg/m²). The pouch was then attached to the ends of the cable of the testing apparatus by fastening the aluminum clamp bars to carabiner hooks at the cable ends.

Similar to Example 2, the horizontal spacing of the rollers was adjusted so that the wrap angle of the test sample over the rollers was 110 degrees. The tension on the cable was adjusted so that minimal tension was applied to the cable (less than 3 psi (20.68 kPa)). The hydraulic drive was turned on and the sample was pulled vertically back and forth through the rollers for 50,000 cycles. The ballistic fabric sample traversed the rollers completely from end to end, i.e. when the cable had reached its topmost direction of travel, the bottom of the ballistic material sample stack had cleared the topmost roller. After the test cycles were completed, the sample was removed from the nylon pouch and visually examined. It was noted that the front and back surfaces of the sample stack exhibited a small amount of abrasion damage that was most evenly spaced across the surface of the sample. The sample also exhibited some fraying around the top and bottom edges, consistent with the appearance of damage on the edges of used ballistic vests formed from similar materials due to normal wear and tear. Thereafter, the sample was subjected to ballistic testing against 9 mm, 129 grain full metal jacket bullets according to the Military Standard MIL-STD-662F testing conditions and tested for $V_{50}$ performance. Analysis of the ballistic testing results showed that the fabric retained 98% of its $V_{50}$ performance compared to a control sample of the same material that had not been subjected to flexure in the inventive apparatus.

EXAMPLE 4

A flexible fabric test sample was prepared from seventeen layers of GOLD FLEX® fabric (described in Example 3). The layers were cut from a large fabric sheet into square pieces measuring about 15.75 inches (40.0 cm) in both length and width. The layers were stacked together and the edges of the stack were taped together to hold the layers together with strapping tape commercially available from Intertape Polymer Group of Montreal, Canada. The stack was then placed into an environmentally controlled chamber which was held at 50° C. and 60% relative humidity, where it remained for twelve months. After twelve months, the material was removed from the chamber and placed inside the zipper opening of a rip-stop nylon pouch as described in Example 3. The pouch was then attached to the ends of the cable of the testing apparatus by fastening the aluminum clamp bars to carabiner hooks at the cable ends.

Similar to Examples 2 and 3, the horizontal spacing of the rollers was adjusted so that the wrap angle of the test sample over the rollers was 110 degrees. The tension on the cable was adjusted so that minimal tension was applied to the cable (less than 3 psi (20.68 kPa)). The hydraulic drive was turned on and the sample was pulled vertically back and forth through the rollers for 50,000 cycles. The ballistic fabric sample traversed the rollers completely from end to end, i.e. when the cable had reached its topmost direction of travel, the bottom of the ballistic material sample stack had cleared the topmost roller. After the test cycles were completed, the sample was removed from the nylon pouch and subjected to ballistic testing against 9 mm, 129 grain full metal jacket bullets according to the Military Standard MIL-STD-662F testing conditions and tested for $V_{50}$ performance. Analysis of the ballistic testing results showed that the fabric retained 91% of its $V_{50}$ performance compared to a control sample of the same material that was stored under normal room temperature and humidity conditions and had not been subjected to flexure in the inventive apparatus.

EXAMPLE 5

A flexible fabric test sample was prepared from twenty-one layers of SPECTRA SHIELD® SA 3118 polyethylene fabric, commercially available from Honeywell International Inc. (a non-woven, two-ply, 0°/90° fabric; SPECTRA® 3000 fibers; aqueous KRATON® emulsion matrix, 16% by weight of the fabric; areal density: 0.77 lb/ft² (3.76 kg/m²)). The layers were cut from a large fabric sheet into square pieces measuring about 15.75 inches (40.0 cm) in both length and width. The layers were stacked together and placed inside a rip-stop nylon pouch through a zipper opening, as in Example 3. The rip-stop nylon pouch was then attached to the ends of the cable of the testing apparatus by fastening the aluminum clamp bars to carabiner hooks at the cable ends.

Figures 5A, 5B:
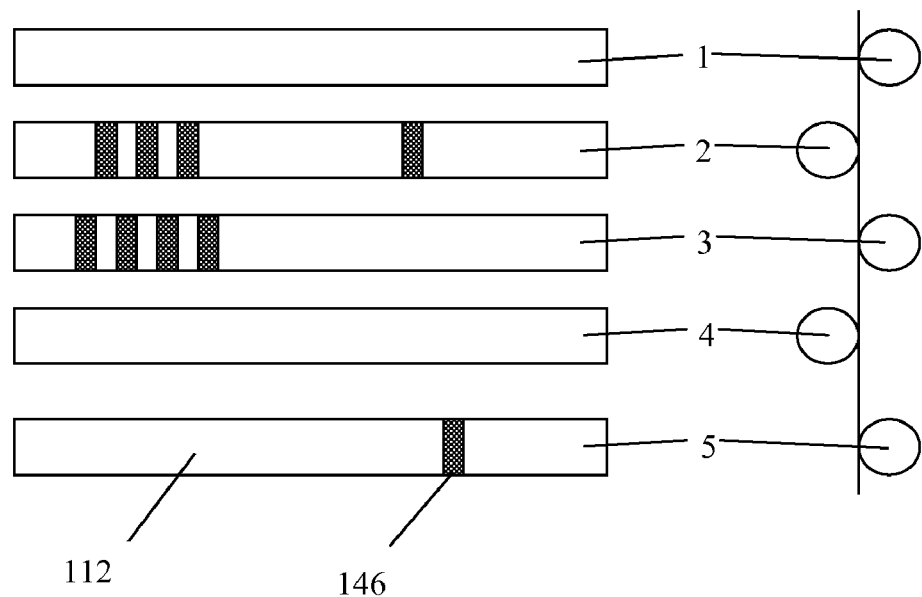
FIG. 5A is a front-view schematic representation of roller assembly including ribbed rollers around the circumference of the rollers.
FIG. 5B is a side-view schematic representation of the roller assembly from FIG. 5A, showing the roller positions.

The fabric sample was tested in a hydraulic powered testing apparatus of the invention including a roller assembly having five rollers, as illustrated in FIGS. 5A and 5B. In this example, the outer surface of the center roller, no. 3, was modified to have a raised, ribbed surface by wrapping the roller with masking tape around its circumference. Particularly, one-inch (2.54 cm) width masking tape was wrapped around the circumference of the center roller to form a raised surface, hereafter referred to as a rib, approximately one-inch high. A total of four ribs were formed along the length of this roller at a spacing of 1⅝ inches (4.13 cm) from one another, where the roller has a radius of three inches (7.62 cm) and a length of twenty-two inches (55.88 cm). The leftmost rib was formed four inches (10.16 cm) from the left end of this center roller. Similar ribs were formed on roller no. 2 such that they were aligned in an offset manner from the ribs on roller no. 3, i.e. the ribs were aligned with the gaps between the ribs on the center roller. One rib was also formed on the right side of roller no. 2, 5⅝ inches (14.29 cm) from its right edge, and one rib was formed in an offset position to this rib on roller no. 3, five inches (12.7 cm) from the right edge of the roller. This offset rib pattern was used to mimic actual fabric creasing, but other patterns are acceptable as well.

Similar to Examples 2 and 3, the horizontal spacing of the rollers was adjusted so that the wrap angle of the test sample over the rollers was 110 degrees. The tension on the cable was adjusted so that minimal tension was applied to the cable (less than 3 psi (20.68 kPa)). The hydraulic drive was turned on and the sample was pulled vertically back and forth through the rollers for 10,000 cycles. The ballistic fabric sample traversed the rollers completely from end to end. After the test cycles were completed, the sample was removed from the nylon pouch and visually examined. The effect of the offset ribs on the sample was very apparent. The damage after 10,000 cycles (at 1 cycle per 6-8 seconds (12-17 inches/second)) exceeded the damage observed after on the other tested samples after 50,000 at the same cycle velocity. The sample exhibited set wrinkles, which were very similar in appearance to wrinkles induced in a used ballistic vest in areas where the vest is constrained by holsters or equipment belts. The sample also exhibited delamination and fiber dislocations in these areas, and the damage extended through the entire thickness of the sample layers.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An apparatus for testing a frictional wear property of a flexible fabric comprising:
   a) a stationary roller assembly comprising a supporting frame, and a plurality of adjacently spaced rollers mounted on the supporting frame; each roller having a central longitudinal axis that is positioned parallel to the central longitudinal axis of the other roller or rollers; each of said rollers being mounted on the supporting frame for rotation around its central longitudinal axis; wherein adjacent rollers are spaced from each other to define a space therebetween that allows a flexible fabric to be translated therethrough; the supporting frame being either attached to or an integral component of a structural framework;
   b) at least two opposing mounts for releasably supporting a flexible fabric to be tested in the space or spaces between adjacent rollers and in a position for frictional engagement of the flexible fabric with the rollers; and
   c) a reciprocating driver connected to the mounts for automatically and continuously translating the mounts back and forth along a path such that when a flexible fabric is supported by the mounts, the flexible fabric is positioned for passing through the space or spaces between the plurality of rollers and in frictional engagement with the rollers.

2. The apparatus of claim 1 wherein at least two adjacent rollers are positioned at an offset position relative to one another such that when a flexible fabric is supported by the mounts, the flexible fabric is positioned at an angle of from about 1 degree to about 180 degrees relative to the rollers.

3. The apparatus of claim 1 wherein at least two adjacent rollers are positioned at an offset position relative to one another such that when a flexible fabric is supported by the mounts, the flexible fabric is positioned at an angle of from about 45 degrees to about 180 degrees relative to the rollers.

4. The apparatus of claim 1 wherein the roller assembly comprises at least four adjacently spaced rollers mounted on the supporting frame, wherein said rollers are sequentially offset from each other.

5. The apparatus of claim 1 wherein the at least two opposing mounts are positioned such that at least one mount is positioned at each of two opposite sides of the roller assembly.

6. The apparatus of claim 1 wherein the reciprocating driver automatically and continuously translates the mounts back and forth along a substantially straight linear path.

7. The apparatus of claim 1 wherein said reciprocating driver includes a drive motor operatively connected to a pneumatic control system for translating the mounts back and forth along the path.

8. The apparatus of claim 1 wherein the structural framework further comprises at least one path-limiting stopper on at least one side of the roller assembly.

9. The apparatus of claim 1 further comprising a flexible carrier pouch releasably connected to the opposing mounts, and the flexible carrier pouch supporting the flexible fabric in the space or spaces between the rollers.

10. The apparatus of claim 9 wherein the flexible fabric is stitched to the flexible carrier pouch.

11. The apparatus of claim 1 wherein each of the opposing mounts are connected to the structural framework by at least one connector element.

12. The apparatus of claim 11 wherein said connector element comprises a connecting wire or connecting cable loop.

13. A process for evaluating a frictional wear property of a flexible fabric, comprising:
   a) providing a roller assembly comprising a supporting frame and a plurality of adjacently spaced rollers mounted on the supporting frame; each roller having a central longitudinal axis that is positioned parallel to the central longitudinal axis of the other roller or rollers; each of said rollers being mounted on the supporting frame for rotation around its central longitudinal axis; wherein adjacent rollers are spaced from each other to define a space therebetween that allows a flexible fabric to be translated therethrough; the supporting frame being either mounted on, attached to or an integral component of a structural framework;
   b) positioning a flexible fabric through the space or spaces between adjacent rollers, which flexible fabric is releasably supported in said space or spaces between adjacent rollers and in a position for frictional engagement with the rollers, by at least two opposing mounts; and
   c) effecting an automatic and continuous reciprocating translation of the flexible fabric back and forth through the space or spaces between the adjacent rollers along a path, under conditions sufficient to cause wear of the flexible fabric.

14. The process of claim 13 further comprising d) measuring the wear of the flexible fabric.

15. The process of claim 13 wherein said flexible fabric comprises multiple fabric layers.

16. The process of claim 13 wherein the roller assembly comprises at least four adjacently spaced rollers mounted on the supporting frame, wherein said rollers are sequentially offset from each other.

17. The process of claim 13 wherein the at least two opposing mounts are positioned such that at least one mount is positioned at each of two opposite sides of the roller assembly.

18. The process of claim 13 wherein a reciprocating driver automatically and continuously translates the mounts back and forth along a substantially straight linear path.

19. The process of claim 13 wherein step b) is conducted by automatic and continuous reciprocating movement of the mounts.

20. The process of claim 13 wherein step b) is conducted by automatic and continuous reciprocating movement of the roller assembly.

21. The process of claim 13 wherein the flexible fabric is translated back and forth through the space between the spaced rollers at least about 10,000 times in each of said back and forth directions, causing wear of the flexible fabric.

22. The process of claim 13 wherein the supporting frame is either attached to or an integral component of a structural framework.

23. The process of claim 13 wherein said flexible fabric is contained within a flexible carrier pouch that is releasably connected to the opposing mounts, and the flexible carrier pouch being positioned in the space or spaces between the rollers.

24. The process of claim 23 wherein the flexible fabric is stitched to the flexible carrier pouch.

25. An apparatus for testing a frictional wear property of a flexible fabric comprising:
   a) a roller assembly comprising a supporting frame and a plurality of adjacently spaced rollers mounted on the supporting frame; each roller having a central longitudinal axis that is positioned parallel to the central longitudinal axis of the other roller or rollers; each of said rollers being mounted on the supporting frame for rotation around its central longitudinal axis; wherein adjacent rollers are spaced from each other to define a space therebetween that allows a flexible fabric to be translated therethrough; the supporting frame being mounted on a structural framework;

b) at least two opposing stationary mounts for releasably supporting a flexible fabric to be tested in the space or spaces between adjacent rollers and in a position for frictional engagement of the flexible fabric with the rollers; and c) a reciprocating driver connected to the roller assembly for automatically and continuously translating the roller assembly back and forth along a path such that when a flexible fabric is supported by the mounts, the flexible fabric is positioned for passing through the space or spaces between the plurality of rollers and in frictional engagement with the rollers.

\* \* \* \* \*